United States Patent [19]
Garber

[11] Patent Number: 5,725,587
[45] Date of Patent: Mar. 10, 1998

[54] ACETABULAR CUP ASSEMBLY

[75] Inventor: Frank D. Garber, Pierceton, Ind.

[73] Assignee: Zimmer, Inc., Warsaw, Ind.

[21] Appl. No.: 572,459

[22] Filed: Dec. 14, 1995

[51] Int. Cl.$^6$ ........................................................ A61F 2/34
[52] U.S. Cl. ................................................ 623/22; 623/18
[58] Field of Search ............................. 623/16, 18, 19, 623/22, 23

[56]  References Cited

U.S. PATENT DOCUMENTS

| | | | |
|---|---|---|---|
| 3,813,699 | 6/1974 | Giliberty | 623/22 |
| 3,916,451 | 11/1975 | Buechel et al. | 623/22 |
| 4,172,296 | 10/1979 | D'Errico | 623/22 |
| 4,279,041 | 7/1981 | Buchholz | 623/22 |
| 4,624,674 | 11/1986 | Pappas et al. | 623/22 |
| 4,718,911 | 1/1988 | Kenna | 623/22 |
| 4,770,659 | 9/1988 | Kendall | 623/22 |
| 5,074,881 | 12/1991 | Thull et al. | 623/22 |
| 5,171,285 | 12/1992 | Broderick | 623/22 |
| 5,222,984 | 6/1993 | Forte | 623/22 |
| 5,282,864 | 2/1994 | Noiles et al. | 623/18 |
| 5,314,487 | 5/1994 | Schryver et al. | 623/22 |
| 5,358,532 | 10/1994 | Evans et al. | 623/22 |
| 5,383,938 | 1/1995 | Rohr et al. | 623/22 |

*Primary Examiner*—Debra S. Brittingham
*Attorney, Agent, or Firm*—Margaret L. Geringer

[57] ABSTRACT

An acetabular cup assembly 10 that uses the mating contour of its bearing component 20 and its shell component 30 to provide a reliable interlocking engagement to secure the bearing component to the shell component is disclosed. Bearing component 20 includes end surface 24 and a convex spherical surface 22, which extends beyond its lateral diametrical plane 23, making the shape of the bearing component slightly greater than a hemisphere. Shell component 30 includes a concave inner surface 36 defining an open cavity 37 for receiving bearing component 20. Concave shell surface 36 has a diametrical recess 40, and surface 36 is complimentary and approximately the same in contour and radial dimension to convex bearing surface 22. Concave shell surface 36 includes an annular portion 38, which extends beyond its lateral diametrical plane 39. Consequently, bearing component 30 can not be inserted directly into the shell cavity, because its lateral diameter is greater than the diameter at the mouth of the shell cavity. Recess 40 in concave shell surface 36 allows bearing component 20 to be inserted into shell cavity 37 in a sideways position. Once inserted in shell cavity 37 in a sideways position, bearing component 20 can be rotated back 90° within the shell cavity so that convex bearing surface 22 is seated concentrically over concave shell surface 36. In this rotated position, annular portion 38 of concave shell surface 36 converges partially over bearing component 20 to secure the bearing component within shell cavity 37.

9 Claims, 3 Drawing Sheets

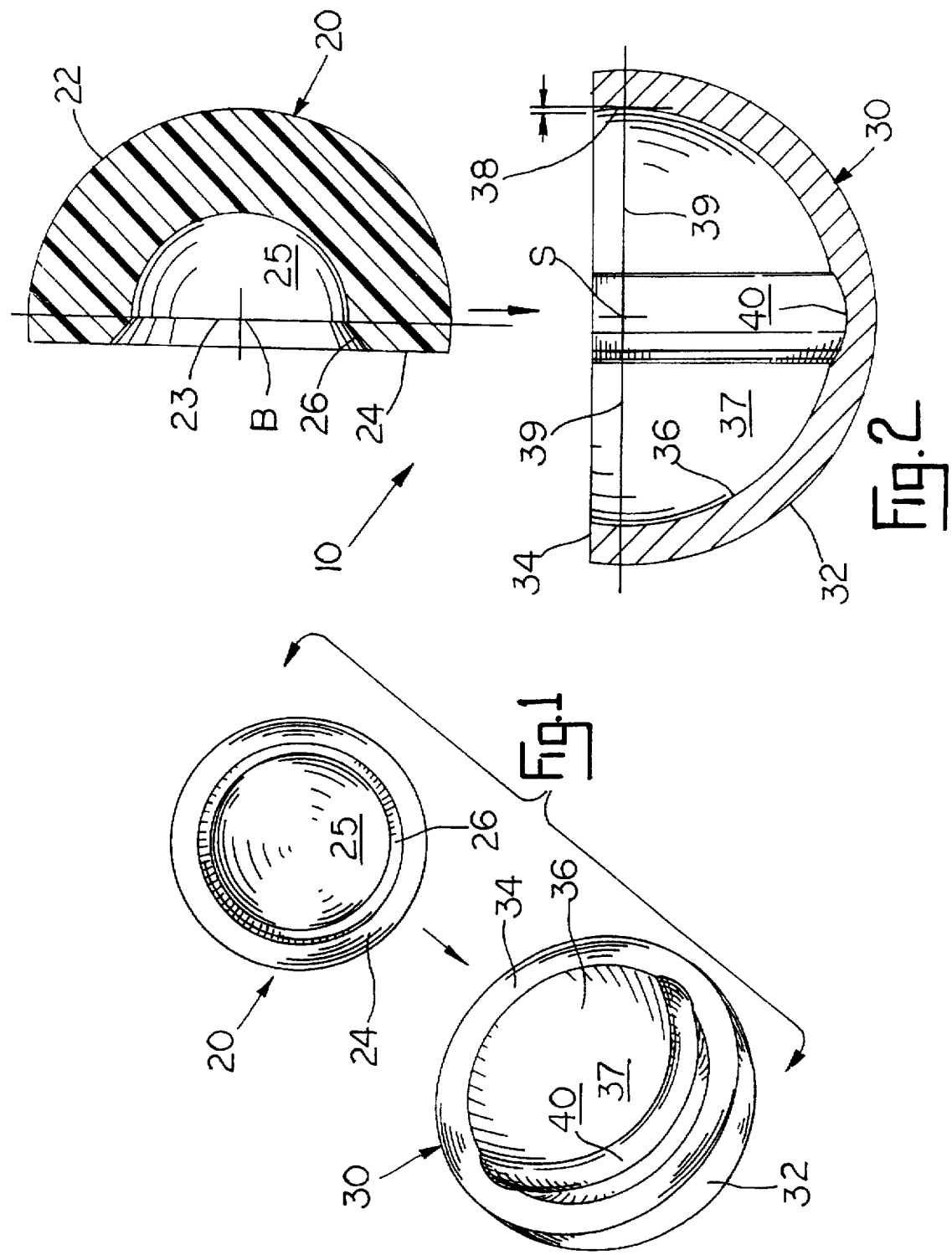

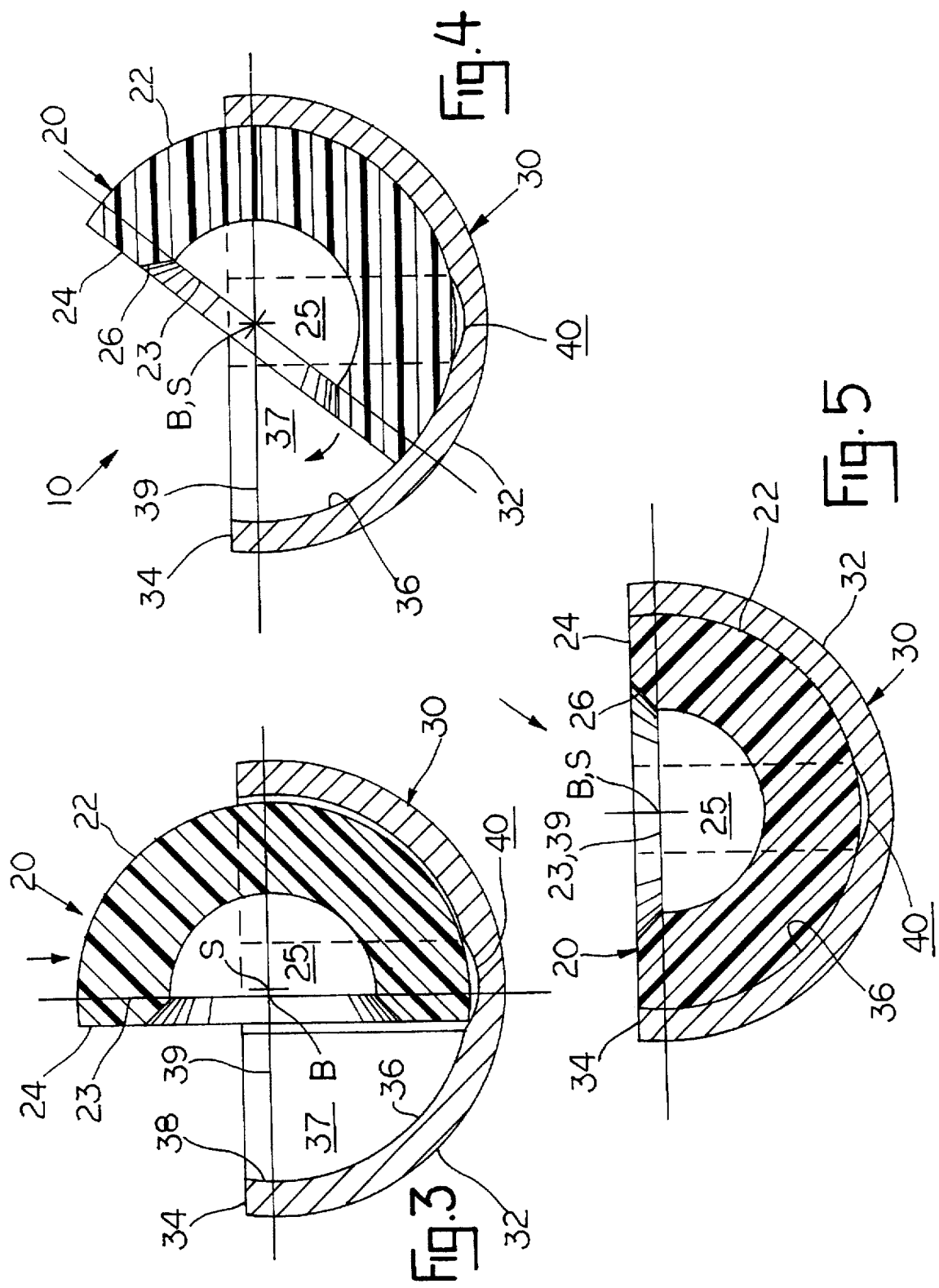

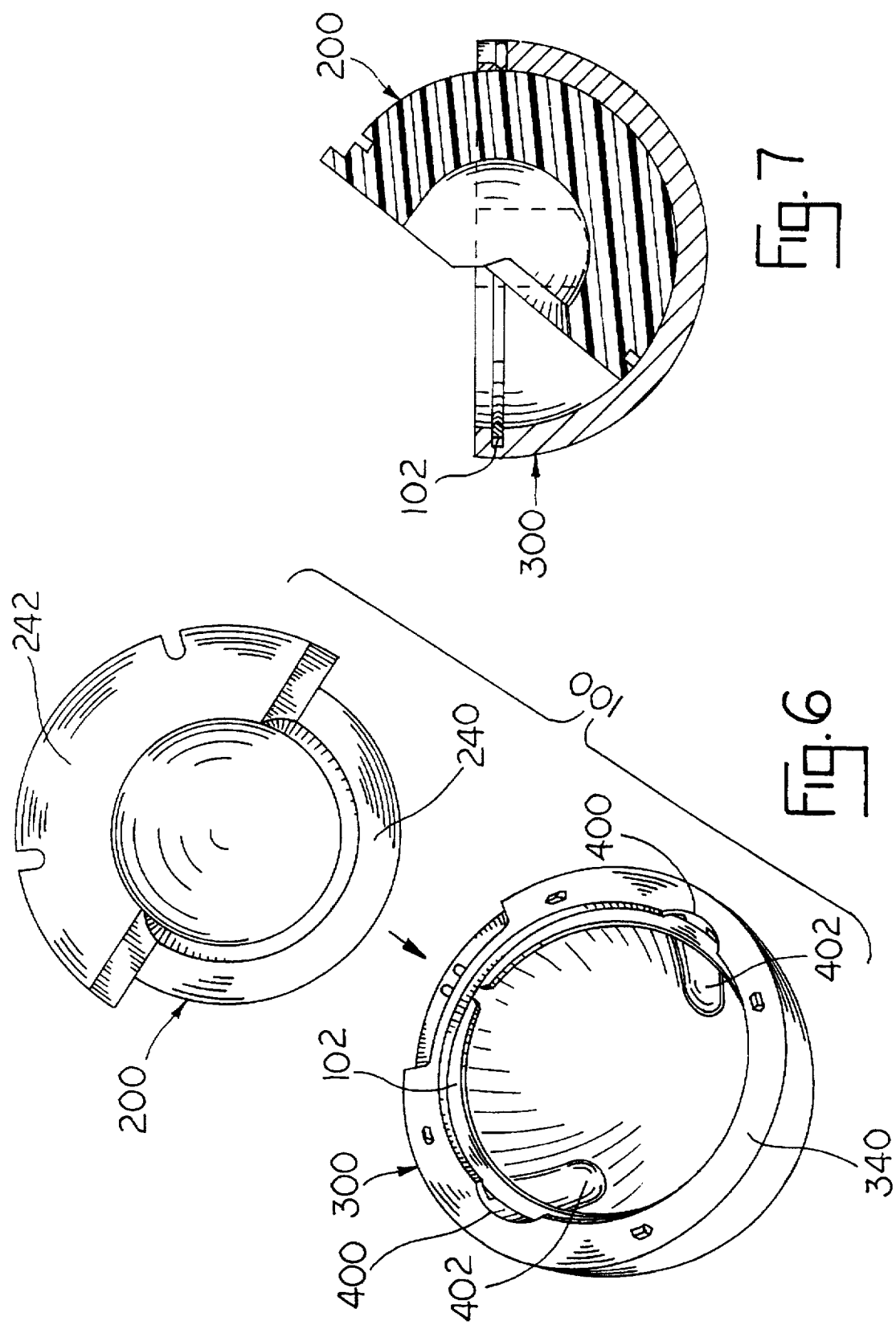

ACETABULAR CUP ASSEMBLY

This invention relates to an acetabular cup assembly, and has specific relevance to the mechanism used to secure the bearing component to the shell component.

BACKGROUND OF THE INVENTION

Prosthetic acetabular cup assemblies are well known in the medical industry for replacing a portion of a patient's hip joint during total hip arthroplasty. Generally the acetabular cup assembly includes a metal shell and a polyethylene bearing component. The bearing components are secured within the shell components by a variety of mechanisms. For example, U.S. Pat. Nos. 5,171,285 and 5,383,938 disclose the use of a snap or lock ring to secure being liners within cup shells. U.S. Pat. No. 5,282,864 to Noiles et al. discloses the use of threaded screws to seat the bearing liner within the shell. Each of these securement mechanisms require additional components and manufacturing to the completed cup assembly.

SUMMARY OF THE INVENTION

The acetabular cup assembly of this invention uses the mating contour of the bearing component and shell component to provide a reliable interlocking engagement, which secures the bearing component to the shell component. No additional components, such as snap rings or fasteners are necessary to secure the bearing component to the shell component. However, such additional securing components could be used if additional securement is desired. In addition, the interlocking engagement used to secure the components of this invention requires less machining and fabricating. The secure interlocking engagement of the bearing and shell may help reduce micromotion between the components.

The cup assembly includes a shell component and bearing component. The bearing component is generally hemispherical in shape and includes a convex spherical surface and an end surface. The convex bearing surface extends beyond its lateral diametrical plane, making the shape of the bearing component slightly greater than a hemisphere. The shell component has a cotyloid shape and includes a spherical concave inner surface defining an open cavity for receiving the bearing component. The concave shell surface is complimentary and approximately the same in contour and radial dimension to the convex bearing surface. The concave shell surface includes an annular portion, which extends beyond its lateral diametrical plane. Consequently, the diameter at the mouth of the shell cavity is less than the over all lateral diameter of the shell cavity. The concave shell surface also has a diametrical recess. The diametrical recess may be a single continuous diametrical recess extending from one side of the inner edge of the shell rim to the opposite side of the inner edge of the shell rim. Alternatively, the dimetrical recess may be a discontinuous diametrical recess including at least two portions, one extending from one side of the inner edge of the shell rim and the other extending from the opposite side of the inner edge of the shell rim, with both portions diametrically aligned with each other.

The bearing component can not be inserted directly into the shell cavity, because its lateral diameter is greater than the diameter at the mouth of the shell cavity. The diametrical recess in the concave shell surface allows the bearing component to be inserted into the shell cavity in a sideways position. With the bearing component rotated 90° about a lateral diametrical axis so that the end surface of the bearing component, which may be a substantially flat end or which may include an elevated lip on the end surface, is substantially perpendicular to the diametrical plane of the concave shell surface and substantially parallel to the recess, the bearing component can be inserted in the shell cavity. The depth and width of the recess allows sufficient lateral clearance for the bearing component in this sideways position. Once inserted in the shell cavity in a sideways position, the bearing component can be rotated back 90° about its diametrical axis within the shell cavity so that the convex bearing surface is seated concentrically over the concave shell surface. When the bearing component is rotated to this final position, the annular portion of the concave shell surface converges partially over the bearing component to secure the bearing component within the shell cavity.

Accordingly, an advantage of the acetabular cup assembly of this invention is that the components are self-interlocking while requiring minimal machining or fabricating.

Another advantage of the present invention is that no instruments are needed to facilitate the securement of the liner within the shell, thereby reducing the instrument count of the surgical procedure; however, a suitable assembly instrument could be provided if desired.

Another advantage of the present invention is that no snap ring is needed to lock the liner in place within the shell; although, a typical lock ring, or other suitable stop-type mechanism could be used in conjunction with the present invention for additional securement, if desired.

Other advantages will become apparent upon a reading of the following description.

BRIEF DESCRIPTION OF THE DRAWINGS

A preferred embodiment of the invention has been depicted for illustrative purposes only wherein:

FIG. 1 is a perspective view of the cup assembly using the locking mechanism of this invention showing the bearing liner positioned for insertion above the shell component;

FIG. 2 is a side sectional view of the cup assembly of FIG. 1 showing the bearing liner positioned for insertion above the shell component;

FIG. 3 is a side sectional view of the cup assembly showing the bearing liner inserted into the shell component in its initial position;

FIG. 4 is a side sectional view of the cup assembly showing the bearing liner pivoting within the shell component;

FIG. 5 is a side sectional view of the cup assembly showing the bearing liner secured in its locked position within the shell component;

FIG. 6 is a perspective view of an alternate embodiment of the cup assembly and locking mechanism of this invention showing the bearing liner positioned for insertion above the shell component; and FIG. 7 is a side sectional view of the cup assembly of FIG. 6 showing the bearing liner pivoting within the shell component.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

The modular acetabular cup assembly 10 of this invention is illustrated in the figures as including a bearing component 20 and a cup or shell component 30. Bearing component 20 is generally hemispherical in shape and includes a convex spherical surface 22 and a flat end surface 24. The locus of spherical bearing surface 22 is equidistant from a center point B. As shown best in FIG. 2, convex bearing surface 22 extends beyond its lateral diametrical plane 23, making the shape of bearing component 20 slightly greater than a hemisphere. End surface 24 has a central opening 25 and a chamfered edge 26 around opening 25 for receiving the head of a conventional hip stem (not shown). Shell component 30 has a cotyloid shape and includes a convex outer surface 32, a spherical concave inner surface 36 and an annular rim 34 defining an open cavity 37 for receiving bearing component 20. Concave shell surface 36 also has a diametrical recess 40. As shown in the FIGS. 2-5, concave shell surface 36 is equidistant from a center point S and is approximately the same in contour and radial dimension to convex bearing surface 22. Concave shell surface 36 includes an annular portion 38 adjacent rim 34, which extends beyond its lateral diametrical plane 39. Consequently, the contour of shell cavity 37 is shaped slightly greater than a hemisphere and is approximately the same as the shape of bearing component 20. Since, annular portion 38 of concave shell surface 36 converges slightly, the diameter at the mouth of shell cavity 37 is less than the over all lateral diameter of the shell cavity.

FIGS. 2-5 illustrate the procedure for affixing bearing component 20 to shell component 30 within shell cavity 37. Bearing component 20 can not be inserted directly into shell cavity 37, because its lateral diameter is greater than the diameter at the mouth of shell cavity 37. As shown in FIG. 2, shell recess 40 allows bearing component 20 to be inserted into shell cavity 37 in a sideways position. As shown in FIGS. 2 and 3, bearing component 20 is rotated 90° about a lateral diametrical axis so that end surface 24 is substantially perpendicular to diametrical plane 39 and positioned substantially parallel to recess 40. The diametrical recess 40 is a single continuous diametrical recess extending from one side of the inner edge of the shell rim 34 to the opposite side of the inner edge of the shell rim. The depth and width of recess 40 allows sufficient lateral clearance for bearing component 20 in this sideways position. As shown in FIGS. 3-5, center point B of convex bearing surface 22 is located at center point S of concave shell surface 36 when bearing component 20 is inserted into shell cavity 37. With the lateral edge of bearing component 20 inserted within recess 40, the bearing component is rotated back 90° about a diametrical axis through center points B.S so that convex bearing surface 22 is seated concentrically over concave shell surface 36 and bearing end face 24 is flush with shell rim 34. When bearing component 20 is rotated to this final position, annular portion 38 of concave shell surface 36 converges partially over bearing component 20 to secure the bearing component within shell cavity 37. One skilled in the art will note that the dimensional tolerances of concave shell surface 36 and spherical bearing surface 22 are critical to a secure concentric engagement between bearing component 20 and shell component 30.

While annular portion 38 of concave shell surface 36 provides a secure interlocking engagement of the bearing component, a conventional lock ring mechanism may also be incorporated into the design of the cup assembly for additional securement, if desired. Such a lock ring 102 is shown in the alternate embodiment of the cup assembly 100 in FIGS. 6 and 7. This cup assembly utilizes a lock ring 102, such as the type described in U.S. Pat. No. 5,383,938, which is incorporated herein by reference. Alternate additional securing mechanisms may also be incorporated, as desired.

In addition, cup assembly 100 includes a diametrical recess 400 which is a discontinuous diametrical recess, including two portions 402, one extending from one side of the inner edge of the shell rim 340 of shell 300 and the other extending from the opposite side of the inner edge of the shell rim, with both portions 402 diametrically aligned with each other. The depth and width and length of recess portions 402 allows sufficient lateral clearance for bearing component 200 to be inserted into the shell 300 in a sideways position.

Also, bearing component 200 shows an end surface 240 with an elevated rim 242 shown thereon. Such elevated rims are known in the art. The bearing component 200, with elevated rim 242, would be inserted into shell 300 with the side opposite the rim 242 being inserted first into the shell in a sideways position. The bearing component 200 is shown in FIG. 7 being rotated or pivoted toward its final position (not shown) in which the lock ring 102 will engage bearing 200 to further secure the assembly of the bearing 200 and shell 300.

It is also noted that the outer surface of the shell may include a porous surface or the shell may include through holes therein. Although these options are not shown, they are well known in the art.

It is understood that the above description does not limit the invention to the details given, but may be modified within the scope of the following claims.

I claim:

1. A modular acetabular cup assembly comprising:

a shell component including a concave spherical surface terminating in an annular rim to define an open inner cavity, said shell concave surface having a recess defined therein and an annular surface portion extending radially beyond the lateral diametrical plane of said shell concave surface, and a bearing component including an end surface and a convex spherical surface having a contour complimentary to said shell concave surface for concentric engagement therewith, said bearing component being insertable into said shell inner cavity in a first position wherein the lateral diametrical plane of said bearing convex surface is sideways or not parallel to the lateral diametrical plane of said shell concave surface and said bearing end surface is positioned over said recess for insertion therein, and being rotatable within said shell inner cavity to a second position wherein said bearing convex surface is seated concentrically over said shell concave surface and said shell surface portion converges partially over said bearing component to secure said bearing component within said shell inner cavity.

2. The cup assembly of claim 1 wherein said recess is a single continuous recess extending from a one inner side of the rim to an opposite inner side of the rim.

3. The cup assembly of claim 1 wherein said recess is a discontinuous recess including at least two portions, a first recess portion extending from a one inner side of the rim and a second recess portion extending from an opposite inner side of the rim, the first and second recess portions being diametrically aligned.

4. The cup assembly of claim 1 wherein said shell rim and said bearing end surface substantially planarly align when said bearing component is seated within said shell cavity in said second position.

5. The cup assembly of claim 1 wherein said bearing concave surface extends radially beyond its lateral diametrical plane.

6. The cup assembly of claim 1 wherein said assembly includes an additional securing means between the shell component and the bearing component.

7. The cup assembly of claim 1 wherein said end surface of said bearing component includes an elevated rim on a portion of the end surface.

8. A modular acetabular cup assembly comprising:

- a shell component including a concave spherical surface terminating in an annular rim to define an open inner cavity, said shell concave surface having a diametrical recess defined therein and an annular surface portion extending radially beyond the lateral diametrical plane of said shell concave surface, and

- a bearing component including an end surface and a convex spherical surface having a contour complimentary to said shell concave surface for concentric engagement therewith,

- said bearing component being insertable into said shell inner cavity in a first position wherein the lateral diametrical plane of said bearing convex surface is substantially perpendicular to the lateral diametrical plane of said shell concave surface and said bearing end surface is positioned over and substantially parallel to said recess, and being rotatable within said shell inner cavity to a second position wherein said bearing convex surface is seated concentrically over said shell concave surface and said shell surface portion converges partially over said bearing component to secure said bearing component within said shell inner cavity.

9. A method of assembling a modular cup assembly wherein said assembly comprises a shell component including a concave spherical surface terminating in an annular rim to define an open inner cavity, said shell concave surface having a recess defined therein and an annular surface portion extending radially beyond the lateral diametrical plane of said shell concave surface, and a bearing component including an end surface and a convex spherical surface having a contour complimentary to said shell concave surface for concentric engagement therewith, and wherein the method comprises:

- inserting said bearing component into said shell inner cavity in a first position wherein the lateral diametrical plane of said bearing convex surface is sideways or not parallel to the lateral diametrical plane of said shell concave surface, and said bearing end surface is positioned over said recess for insertion therein; and

- rotating said bearing component within said inner cavity to a second position wherein said bearing convex surface is seated concentrically over said shell concave surface and said shell surface portion converges partially over said bearing component to secure said bearing component within said shell inner cavity.

* * * * *